(12) United States Patent
Raichle et al.

(10) Patent No.: US 8,609,899 B2
(45) Date of Patent: *Dec. 17, 2013

(54) PROCESS FOR PREPARING TOLUENEDIAMINE BY HYDROGENATION OF DINITROTOLUENE

(75) Inventors: Andreas Raichle, Dresden (DE); Joana Coelho Tsou, Bruessel (BE); Samuel Neto, Brussels (BE); Ulrich Penzel, Tettau (DE); Steffen Oehlenschlaeger, Antwerp (BE); Michael Zoellinger, Eislingen (DE); Holgar Braunsberg, Senftenberg (DE); Stefanie Haase, Bretnig-Hauswalde (DE); Johannes Buettner, Ruhland (DE)

(73) Assignee: BASF SE, Ludwigshafen (DE)

( * ) Notice: Subject to any disclaimer, the term of this patent is extended or adjusted under 35 U.S.C. 154(b) by 13 days.

This patent is subject to a terminal disclaimer.

(21) Appl. No.: 13/109,399

(22) Filed: May 17, 2011

(65) Prior Publication Data

US 2011/0295039 A1 Dec. 1, 2011

Related U.S. Application Data

(60) Provisional application No. 61/345,167, filed on May 17, 2010.

(51) Int. Cl.
*C07C 209/00* (2006.01)
(52) U.S. Cl.
USPC .......................... 564/420; 564/415; 564/416
(58) Field of Classification Search
None
See application file for complete search history.

(56) References Cited

U.S. PATENT DOCUMENTS

| 6,350,911 B1 | 2/2002 | Sander et al. |
| 6,677,271 B1 | 1/2004 | Birke et al. |
| 6,680,280 B1 | 1/2004 | Birke et al. |
| 2010/0130788 A1 | 5/2010 | Coelho Tsou et al. |

FOREIGN PATENT DOCUMENTS

| DE | 198 44 901 | 11/1999 |
| EP | 1 161 297 A0 | 12/2001 |
| EP | 1 165 231 A0 | 1/2002 |
| WO | WO 00/35852 | 6/2000 |
| WO | WO 2008/138784 A1 | 11/2008 |
| WO | WO 2010/015667 A1 | 2/2010 |
| WO | WO 2010/076251 A1 | 7/2010 |
| WO | WO 2010/097453 A1 | 9/2010 |
| WO | WO 2010/149544 A2 | 12/2010 |

OTHER PUBLICATIONS

U.S. Appl. No. 13/057,869, filed Jul. 5, 2011, Penzel, et al.
U.S. Appl. No. 13/142,718, filed Jun. 29, 2011, Coelho Tsou, et al.
U.S. Appl. No. 13/203,360, filed Aug. 25, 2011, Mackenroth, et al.
U.S. Appl. No. 61/220,740, filed Dec. 26, 2011, Schelling, et al.
U.S. Appl. No. 13/380,680, filed Dec. 23, 2011, Schelling, et al.
U.S. Appl. No. 13/362,607, filed Jan. 31, 2012, Allardt, et al.
U.S. Appl. No. 13/421,453, filed Mar. 15, 2012, Waters, et al.
U.S. Appl. No. 13/759,466, filed Feb. 5, 2013, Raichle, et al.

*Primary Examiner* — Clinton Brooks
(74) *Attorney, Agent, or Firm* — Oblon, Spivak, McClelland, Maier & Neustadt, L.L.P.

(57) ABSTRACT

The invention relates to a process for the continuous preparation of toluenediamine by liquid-phase hydrogenation of dinitrotoluene by means of hydrogen in the presence of a suspended, nickel-comprising catalyst in a reactor with a product isolation unit downstream of the reactor to give a product output from the reactor comprising a liquid phase comprising toluenediamine and dinitrotoluene, in which the nickel-comprising catalyst is suspended, wherein the concentration of dinitrotoluene in the liquid phase of the product output from the reactor in the region between the reactor and the downstream product isolation unit is set to a value in the range from 1 to 200 ppm by weight, based on the total weight of the liquid phase of the product output from the reactor.

19 Claims, No Drawings

PROCESS FOR PREPARING TOLUENEDIAMINE BY HYDROGENATION OF DINITROTOLUENE

This patent application claims the benefit of pending U.S. provisional patent application Ser. No. 61/345,167 filed May 17, 2010 incorporated in its entirety herein by reference.

The invention relates to a process for preparing toluenediamine by hydrogenation of dinitrotoluene.

Toluenediamine, hereinafter referred to as TDA, is an aromatic amine which is frequently used in industry; it is, in particular, processed further to give tolylene diisocyanate which is predominantly used in polyurethane production. TDA is prepared industrially by catalytic hydrogenation of dinitrotoluene, hereinafter referred to as DNT.

Many catalysts have been developed for the above reaction in order to achieve a very high yield and selectivity in the reaction and also to discover catalysts which are stable at relatively high reaction temperatures.

The hydrogenation of DNT is strongly exothermic. It has therefore always been an aim to utilize the heat of reaction, for example in the form of steam.

As a reactor which is particularly suitable for removing the heat of reaction, WO 00/35852 A1 has proposed a reactor which has internal and external loop motion and is configured as a vertically upright apparatus having a driving jet nozzle at its upper end, via which the reaction mixture taken off from the reaction bottoms is injected via an exothermic loop into the upper region of the reactor and subsequently flows into a central plug-in tube which is arranged in the longitudinal direction of the reactor, flows through this tube from the top downward, is there deflected by an impingement plate and again flows upward in an internal loop motion outside the plug-in tube. To remove the heat of reaction, heat exchangers, in particular field tubes, i.e. double tubes which are arranged vertically in the longitudinal direction of the reactor and in which the inner tube is open at the lower end to the outer tube and the outer tube is closed off at the bottom from the reaction space and in which a heat transfer medium, in particular water, flows and removes the heat of reaction, are provided in the interior of the reactor. In addition to the removal of heat via heat exchangers arranged in the interior of the reactor, a heat exchanger can also be provided in the external loop flow. In the process described in WO 00/35852 A1, aromatic amines are said to be produced in a high space-time yield and with significant suppression of secondary reactions.

However, it has been found that increased contents of nitroaromatics occasionally occur in the reactor, in particular at the position at which DNT is introduced and in the downward-directed flow, especially when low catalyst contents are used.

DE 198 44 901 C1 describes a process for preparing aromatic amines by the liquid-phase process, in which the nitroaromatics are fed via a ring conduit provided with holes into the reactor. The ring conduit can also be cooled by means of an external heat exchanger in order to rule out the risk of overheating and thus thermal decomposition of the nitroaromatics. In this process, particularly good distribution of the nitroaromatics in the reaction mixture is said to be achieved. Reactors described as suitable are, for example, loop reactors, bubble columns, preferably stirred vessels. The advantages of the process described in DE 198 44 901 C1 is said to be that both catalyst deactivation and by-product formation are significantly reduced.

The challenge in the above processes for preparing TDA is to provide processes in which catalyst deactivation and by-product formation are reduced. It is therefore an object of the present invention to provide an economically attractive process for the catalytic hydrogenation of DNT to TDA which ensures an increased operating life of the catalyst and selectivity of the conversion of DNT into TDA.

The present invention accordingly provides a process for the continuous preparation of toluenediamine by liquid-phase hydrogenation of dinitrotoluene by means of hydrogen in the presence of a suspended, nickel-comprising catalyst in a reactor with a product isolation unit downstream of the reactor to give a product output from the reactor comprising a liquid phase comprising toluenediamine and dinitrotoluene, in which the nickel-comprising catalyst is suspended, wherein the concentration of dinitrotoluene in the liquid phase of the product output from the reactor in the region between the reactor and the downstream product isolation unit is set to a value in the range from 1 to 200 ppm by weight, based on the total weight of the liquid phase of the product output from the reactor.

It has been found that ensuring a minimum DNT concentration of at least 1 ppm, for example by lowering the reaction temperature, the hydrogen partial pressure, the residence time, the catalyst concentration or catalyst activity or by increasing the amount of dinitrotoluene fed in enables by-product formation to be considerably reduced.

Furthermore, it has been found that limiting the DNT concentration to not more than 200 ppm enables catalyst deactivation to be largely avoided.

In summary, it has thus been found that by-product formation can be reduced and at the same time catalyst deactivation can be largely avoided by setting the dinitrotoluene concentration to a value in the range from 1 to 200 ppm.

The dinitrotoluene concentration in the liquid product output from the reactor is preferably set to a value in the range from 1 to 100 ppm by weight, based on the total weight of the liquid product output from the reactor, more preferably to a value of from 2 to 50 ppm by weight, based on the total weight of the liquid product output from the reactor, and particularly preferably to a value in the range from 3 to 30 ppm by weight, based on the total weight of the liquid product output from the reactor.

For the purposes of the invention, "liquid product output in the region between the reactor and the product isolation unit" means a liquid stream or a plurality of liquid streams via which the product output is discharged from the reactor. The product output is preferably discharged at a place of low DNT concentration, i.e. typically at a position facing away from the DNT inlet via a catalyst removal unit. In the case of stirred tank reactors, a simple overflow is frequently utilized as catalyst removal unit for this purpose. In the case of loop reactors, on the other hand, the product output is usually discharged from the external loop.

Ensuring a DNT concentration in the range from 1 to 200 ppm in precisely this "liquid product output in the region between the reactor and the product isolation unit" thus at the same time serves as a final control on the mixing and reaction processes in the preceding reactors. Reference is explicitly made at this point to the technically very much more complicated task of ensuring suitable DNT concentrations at various points directly in the reactor. The concentration ranges to be set would in this case increase considerably with increasing vicinity to the point at which the DNT is introduced (and/or to regions in the reactor in which flow is relatively poor).

The product isolation unit or catalyst removal unit is generally a filter (e.g. a membrane filter/crossflow filter), a static decanter (e.g. a gravity separator or settler, frequently a lamellar clarifier) or a dynamic decanter (e.g. a centrifuge or a jet separator). The catalyst is separated off from the product and is subsequently recirculated (generally as a thickened suspension) to the reactor. The product output is particularly preferably discharged with retention of the catalyst. The amine can then be purified by conventional and known methods, for example by distillation or extraction.

The setting of the DNT concentration in the liquid product output from the reactor in the region between the reactor and the downstream product isolation unit on the basis of a repeated measurement of the dinitrotoluene concentration in the liquid product output from the reactor is carried out at time intervals of ≤24 hours. The measurement is preferably repeated continually at time intervals of ≤12 hours, particularly preferably ≤4 hours and very particularly preferably ≤1 hour. The time intervals employed for monitoring should be selected so that changes in the DNT concentration in the region between the reactor and product isolation unit can be reacted to quickly. The samples to be taken for monitoring are usually taken upstream of the product isolation unit (for example when a settler is used) or downstream of the product isolation unit (for example when a filter is used). The measurement of the DNT concentration can be carried out in-line, on-line or off-line.

As reactors in which the process of the invention can be carried out, it is in principle possible to use all reactors suitable for the continuous hydrogenation of nitroaromatics. Suitable reactors for the process of the invention are continuously operated stirred tank reactors, and circular flow reactors or loop reactors and also bubble columns are likewise suitable. In the process of the invention, preference is given to using stirred tank reactors, loop reactors, bubble columns or jet loop reactors having internal and external circulation, as described, for example, in WO 00/35852 A1.

In the process of the invention, DNT is hydrogenated to TDA. Particularly low by-product formation and catalyst deactivation are observed.

The hydrogenation is carried out in the process of the invention under a pressure in the range from 5 to 50 bar, preferably at a pressure in the range from 10 to 40 bar, particularly preferably at a pressure in the range from 20 to 30 bar. The operating temperature at which the hydrogenation of dinitrotoluene to toluenediamine is carried out is generally in the range from 50 to 250° C., preferably in the range from 80 to 200° C., preferably in the range from 105 to 130° C.

In a further preferred embodiment of the invention, the process of the invention is operated in such a way that the concentration of the partially hydrogenated intermediate aminonitrotoluene, hereinafter referred to as ANT for short, is also controlled and is set in the region between the reactor and the product isolation unit to an ANT concentration in the range from 0 to 2000 ppm, preferably to an ANT concentration in the range from 0.5 to 1000 ppm, particularly preferably to an ANT concentration in the range from 1 to 200 ppm. Setting of the concentration of this partially hydrogenated intermediate in the ranges mentioned firstly allows a further reduction in catalyst deactivation and secondly a further reduction in by-product formation. In general, the concentrations of DNT and ANT run largely parallel.

Many catalysts are possible for the preparation of TDA.

In a first general embodiment of the invention, the process of the invention is, as indicated above, carried out in the presence of a catalyst, in particular in the presence of a supported catalyst comprising, as active component, nickel either alone or together with at least one metal of transition groups I., V., VI. and/or VIII. of the Periodic Table. The catalysts used according to the invention can be produced industrially by applying nickel and optionally at least one of the abovementioned additional metals to a suitable support.

In a preferred embodiment of the invention, the catalyst has a nickel content in the range from 0.1 to 99% by weight, preferably from 1 to 90% by weight, particularly preferably from 25 to 85% by weight and very particularly preferably from 60 to 80% by weight, based on the total weight of the catalyst.

As metals of transition groups I., II., V., VI. and/or VIII. of the Periodic Table, preference is given to using palladium, platinum, rhodium, iron, cobalt, zinc, chromium, vanadium, copper, silver or a mixture of two or more thereof.

In a preferred embodiment of the invention, the catalyst comprises Ni and platinum. In a further preferred embodiment of the invention, the catalyst comprises Ni and Al; in a further particularly preferred embodiment, the catalyst comprises nickel, palladium and iron.

As support materials, preference is given to using activated carbon, carbon black, graphite or oxidic support components such as silicon dioxide, silicon carbide, kieselguhr, aluminum oxide, magnesium oxide, titanium dioxide, zirconium dioxide and/or hafnium dioxide or a mixture of two or more thereof, particularly preferably zirconium dioxide, $ZrO_2$, $HfO_2$ and/or $SiO_2$, $ZrO_2$ and/or $SiO_2$, $ZrO_2$, $HfO_2$.

The supports used are preferably mesoporous and have an average pore diameter of from 35 to 50 nm and a specific surface area of from 50 to 250 $m^2/g$. The surface area of the support is determined by the BET process by means of $N_2$ adsorption, in particular in accordance with DIN 66131. The average pore diameter and the pore size distribution are determined by Hg porosimetry, in particular in accordance with DIN 66133.

The application of nickel and optionally the at least one further metal can be achieved by the customary suitable methods which are known to a person skilled in the field of catalyst technology. The supports which have been coated, coated by coprecipitation or impregnated with the metal or metal salts are subsequently dried and calcined by known methods. The coated supports are subsequently activated by treating them in a gas stream which comprises free hydrogen. This activation usually takes place at temperatures in the range from 30 to 600° C., preferably in the range from 80 to 150° C. and particularly preferably at 100° C. The gas stream preferably comprises from 50 to 100% by volume of hydrogen and from 0 to 50% by volume of nitrogen. The catalyst produced for use according to the invention has a degree of reduction of at least 70% after reduction for one hour at 100° C.

The supported catalysts obtained in this way generally have a nickel metal surface area of from about 10 to about 50 $m^2/g$, preferably from about 20 to about 60 $m^2/g$. The nickel content of the catalysts used in the process of the invention is generally in the range from 0.1 to 99% by weight, preferably in the range from 1 to 90% by weight, particularly preferably in the range from 25 to 85% by weight, based on the total weight of the catalysts used.

Suitable catalysts of this embodiment are described, for example, in the publications EP 1 161 297 A1 and EP 1 165 231 A1.

In a second embodiment of the invention, activated nickel catalysts as described, for example, in WO 2008/145179 A1 are used in the process of the invention. Accordingly, in a preferred embodiment of the invention, activated nickel catalysts based on an Ni/Al alloy, which can comprise one or more metals selected from the group consisting of Mg, Ce, Ti, V, Nb, Cr, W, Mn, Re, Fe, Ru, Co, Rh, Ir, Pt, Cu, Ag, Au and Bi, are used. The degree of doping is in the range from 0.05% by weight to 20% by weight for each doping element. The average particle size of the catalysts used is <25 μm.

In a third embodiment of the invention, catalysts as are described, for example, in WO 2008/138784 A1 are used in the process of the invention. The invention thus further provides, in a preferred embodiment of the invention, for the use of hydrogenation catalysts comprising, as active component, a mixture of nickel, palladium and an additional element selected from the group consisting of cobalt, iron, vanadium, manganese, chromium, platinum, iridium, gold, bismuth, molybdenum, selenium, tellurium, tin and antimony on a support for preparing aromatic amines by catalytic hydrogenation of the corresponding nitro compounds, in particular for preparing toluenediamine by hydrogenation of dinitrotoluene. The additional element is preferably selected from the group consisting of cobalt, iron, vanadium, bismuth and tin.

As supports for the catalysts, it is possible to use the materials which are customary and known for this purpose. Preference is given to using activated carbon, carbon black, graphite or metal oxides, preferably hydrothermally stable metal oxides such as $ZrO_2$, $TiO_2$, $Al_2O_3$. In the case of graphite, HSAG (high surface area graphite) having a surface area of from 50 to 300 $m^2/g$ is particularly preferred. Particular preference is given to activated carbons, in particular physically or chemically activated carbons, or carbon blacks such as acetylene black.

The catalysts according to the invention are produced, for example, by initially charging the support and bringing it into contact with an aqueous solution of the palladium and nickel salts together with the additional element. Here, the amount of the water used for dissolving the salts should be such that a kneadable paste is formed. The water is preferably used in an amount of from 100 to 200% by weight of the mass of the support. As metal salts, use is made, in particular, of nitrates or chlorides, with nitrates being preferred because they are less corrosive. The paste is mixed and the water is then evaporated under reduced pressure at temperatures in the range from 50 to 100° C., for example in a rotary evaporator or in an oven. For safety reasons, the evaporation can be carried out in a stream of nitrogen. Fixing of the metals to the support can be effected when using chlorides as metal salts by reduction by means of hydrogen. However, corrosion can occur here. The metals are therefore preferably fixed under alkaline conditions. This is carried out, in particular, by addition of an aqueous solution of alkali metal carbonates and subsequent washing of the support until it is free of anions. As an alternative, the metals can also be precipitated from a supernatant solution on to the support under alkaline conditions, in particular at a pH in the range from 8 to 9. The support is then dried, preferably as described above, and reduced by means of hydrogen. This can be affected, for example, in a rotary sphere oven. Before removal of the catalyst from the oven, the catalyst is passivated, for example under an inert gas such as nitrogen containing traces of air, preferably not more than 10% by volume.

The hydrogenation catalysts according to the invention produced by this method preferably comprise from 0.5 to 5% by weight of palladium, from 10 to 20% by weight of nickel and from 0.5 to 5% by weight of the additional element.

In a further embodiment of the production of the hydrogenation catalysts used according to the invention, the reduction of the catalysts is effected by addition of salts having a reducing action, e.g. ammonium carboxylates or alkali metal carboxylates, for example ammonium formate or sodium formate. For this purpose, the support is suspended in water and the solutions of the metal salts are added simultaneously with or after suspension. As metal salts, use is made, in particular, of nitrates or chlorides, with nitrates being preferred because they are less corrosive. The salts having a reducing action are added to this solution and the suspension is heated, for example by boiling under reflux. The catalysts are subsequently washed free of anions and filtered, for example by means of a filter press or a centrifuge, and used as moist paste. Further examples of the production of the catalysts which are preferably used may be found in WO 2005/037768 A1.

In the process of the invention, 2,4-DNT or industrial mixtures thereof which further comprise 2,6-DNT, with these mixtures preferably comprising up to 35% by weight, based on the total weight, of 2,6-DNT with proportions of from 1 to 4% of vicinal DNT and from 0.5 to 1.5% of 2,5- and 3,5-DNT, are hydrogenated to the corresponding amine. The DNT isomers are frequently used in the isomer ratio obtained in the dinitration of toluene.

In the process of the invention, the 2,4-DNT or the 2,4-DNT/2,6-DNT mixture can be used in pure form, as a mixture with water, as a mixture with water and an alcoholic solvent or as a mixture with water, an alcoholic solvent and a catalyst-reactivating additive. It is likewise possible for catalysts, water and/or alcoholic solvents or mixtures thereof to be introduced together or separately in addition to and separately from the DNT.

As can be derived from what has been said above, the hydrogenation in the process of the invention can be carried out in the absence or presence of an alcoholic solvent and a catalyst-activating additive.

If an alcoholic solvent and a catalyst-reactivating additive are used, it is of course also possible to add mixtures of two or more thereof.

Alcoholic solvents used are lower aliphatic alcohols having from 1 to 6 carbon atoms, preferably methanol, ethanol or propanol or a mixture of two or more thereof.

As catalyst-activating additives, preference is given to using aprotic solvents, in particular acetone, dimethylformamide, dioxane or tetrahydrofuran or a mixture of two or more thereof.

The amount of the alcoholic solvents used and of the catalyst-reactivating additives is not restricted in any particular way for the purposes of the process of the invention and can be chosen freely by a person skilled in the art in accordance with requirements.

In a preferred embodiment of the invention, the hydrogenation is carried out in a three-phase mixture of hydrogen-comprising gas phase, suspended catalyst and liquid phase comprising from 0 to 40% by volume of an alcohol, from 10 to 60% by volume of water and from 20 to 70% by volume of TDA, as defined above. The catalyst content is from about 0.1 to 15% by weight, preferably from 2 to 8% by weight, based on the total weight of the three-phase mixture used.

The invention is illustrated by the following examples.

EXAMPLES

Example 1

A cylindrical loop reactor having a driving jet nozzle which is driven by two centrifugal pumps connected in series and is arranged centrally at the top of the reactor and opens into an external circuit, a concentric plug-in tube and an impingement plate in the lower part of the reactor for deflecting the loop flow (internal circuit) (for the functional principle, cf. WO 2000/35852 A1) was used. The reaction volume of the reactor was about 14 $m^3$. The reactor was provided with a bundle of field tubes connected in parallel to remove the heat of reaction. The amount of cooling water fed into the field tubes was set so that the temperature in the reactor was maintained at about 120° C. To maintain the loop flow, a volume flow of 600 m³/h was circulated in the external product circuit, as a result of which a pressure drop of about 2.5 bar was established over the driving jet nozzle. The reactor comprised about 12 m³ of a liquid hydrogenation bath. This consisted essentially of a mixture of TDA and water in a mass ratio of 0.58:0.42 in which about 5% by weight of a metallic Ni catalyst supported on $SiO_2$ and $ZrO_2$ (produced as described in example 2 of EP 1 161 297 and comminuted by means of a stirred mill; here, 10% by volume of the catalyst consisted of particles having a diameter of ≤ about 5 µm, 50% by volume are ≤ about 10 µm and 90% by volume are ≤ about 15 µm, measured by laser light scattering (Malvern Mastersizer S) after stirring in water) were suspended and, in addition, hydrogen was dissolved. The liquid surface was just below the opening of the driving jet nozzle. Above this there were about 2 m³ of a gas atmosphere whose hydrogen content was set to from 90 to 95% by volume (in addition to inert gases such as $N_2$) by continuous discharge of a small offgas stream. 7.5 t/h of molten DNT heated to about 80° C., which comprised a mixture of the 2,4- and 2,6-DNT isomers in a ratio of about 80:20 and about 5% of the remaining DNT isomers and traces of mononitrotoluene, was injected into the gas space of the reactor by means of a diaphragm metering pump. A pressure of 25 bar was set in the reactor by simultaneous introduction of about 0.5 t/h of hydrogen (diluted with about 2 kg/h $N_2$). 95% of the hydrogen was metered into the hydrogenation bath via a nozzle ring above the impingement plate and 5% was metered in at the reactor outlet. The reaction proceeded under largely isothermal conditions: the reaction temperature remained in the range from 116 to 126° C. in the overall reactor. In addition, 625 kg/h of a suspension of the abovementioned catalyst in water (partly separated off from the hydrogenation product in the work-up section) were metered in, likewise continuously, by means of a diaphragm pump. The amount of catalyst comprised in this suspension was varied in a targeted manner in the range from 0 to 5 kg/h in order to set the DNT concentration and was on average about 1 kg/h.

To keep the liquid level in the reactor constant, an appropriate amount of hydrogenation product was taken off continuously from the external product circuit on the pressure side of the 2nd centrifugal pump and fed into a lamellar clarifier having a liquid volume of about 50 m³ and a gas volume of about 10 m³. The catalyst could concentrate in the lower region of the clarifier. 18 standard m³/h of an appropriately thickened suspension were then recirculated to the suction side of the 1st centrifugal pump. At the same time, about 8.6 t/h of hydrogenation product were taken from the lamellar clarifier via an overflow. This product comprised about 4.9 t/h of TDA (with an isomer distribution corresponding to that of the DNT used), about 0.1 t/h of low and high boilers (in a ratio of about 20:80) and about 3.6 t/h of water and up to about 1 kg/h of catalyst (mostly fines). The hydrogenation product was conveyed via a pressure reduction like the hydrogenation products of other reactors into a joint intermediate vessel and was from this conveyed continuously to the work-up by distillation. The parts in contact with the product were partly made of standard steel (in general St37) and partly of stainless steel (1.4571).

To determine the content of DNT and ANT in the hydrogenation bath, samples of suspension were taken at intervals of not more than 4 hours from the line from the external product circuit of the loop reactor to the lamellar clarifier. These were freed of suspended solid by filtration and the concentration of the nitro compounds comprised was determined by means of polarography. The DNT concentration was set to from 3 to 30 ppm (on average: 10 ppm) and the ANT concentration was set to from 1 to 200 ppm (on average: 3 ppm) by adjusting the catalyst concentration in the aqueous suspension fed to the reactor (see above).

The reactor was operated under the conditions mentioned for 3 months without significant interruptions. During this time, the crystallite size determined by means of X-ray powder diffraction of the Ni catalyst filtered off in each case from the above samples of suspension increased from 9 nm to 14 nm as a result of sintering. During a further three months under these conditions, the crystallite size increased further to 15 nm. An appreciable change in the stoichiometric composition of the catalyst or its catalytic performance was not observed over the entire 6 months, nor was formation of oxidized Ni species (for example formation of $Ni(OH)_2$ by oxidative poisoning).

Example 2

A stirred tank reactor (diameter: 2.8 m, height: 4.7 m, volume: 23 m³, material: St37) having cooling coils fastened by means of fine supports in the interior in the region of the reactor wall and a double inclined blade stirrer was used: the larger upper set of inclined blades pushed the hydrogenation bath downward in the interior of the reactor, and the bath then flowed upward again along the cooling coils; the lower set of inclined blades, on the other hand, sucked in the thickened suspension flowing back from the lamellar clarifier which was likewise used here and pushed it upward into the flow generated by the upper set of blades. The amount of cooling water fed into the cooling coils was set so that the temperature in the reactor was maintained in the range from 116 to 126° C. The reactor comprised about 18 m³ of a liquid hydrogenation bath. This consisted essentially of a mixture of TDA and water in a mass ratio of 0.58:0.42 in which about 5% by weight of the metallic Ni catalyst supported on $SiO_2$ and $ZrO_2$, as mentioned in example 1, was suspended and, in addition, hydrogen was dissolved. Above the surface of the liquid there was about 5 m³ of a gas atmosphere whose hydrogen content was set to from 90 to 99% by volume (in addition to inert gases such as $N_2$) by continuously discharging a small offgas stream.

5 t/h of molten DNT heated to about 80° C., which consisted of a mixture of the 2,4- and 2,6-DNT isomers in a ratio of about 80:20 and about 5% of the other DNT isomers and traces of mononitrotoluene, were metered by means of a diaphragm metering pump into a funnel which was open in the direction of the gas space and conveyed the DNT downward via a line into the hydrogenation bath between the sets of inclined blades. A pressure of 25 bar was set in the reactor by simultaneous introduction of about 330 kg/h of hydrogen (diluted with about 2 kg/h of $N_2$). The hydrogen was metered into the hydrogenation bath via a nozzle ring which was installed centrally between the two sets of inclined stirrer blades and fastened there by means of frame supports. The reaction proceeded under largely isothermal conditions. In addition, 435 kg/h of a suspension of the abovementioned catalyst in water (partly separated off from the hydrogenation product in the work-up section) were metered in, likewise continuously, by means of a diaphragm pump. The amount of the catalyst comprised in the suspension was varied in a targeted manner in the range from 0 to 5 kg/h to set the DNT concentration and was on average just under 1 kg/h.

To keep the liquid level of the reactor constant, an appropriate amount of hydrogenation product was taken off continuously via an overflow and fed into a lamellar clarifier having a liquid volume of about 16 m³ and a gas volume of about 4 m³. The catalyst could concentrate in the lower region of the clarifier. About 30 standard m³/h of an appropriately thickened suspension were then sucked back into the stirred tank by means of the lower set of blades of the inclined blade stirrer. At the same time, about 5.8 t/h of hydrogenation product were taken from the lamellar clarifier via an overflow. This product comprised about 3.3 t/h of TDA (with an isomer distribution corresponding to that of the DNT used), about 0.07 t/h of low and high boilers (in a ratio of about 10:60) and about 2.4 t/h of water and up to 1 kg/h of catalyst (mostly fines). The hydrogenation product was conveyed via a pressure reduction like the hydrogenation products of other reactors into a joint intermediate vessel and from this was fed continuously to the work-up by distillation.

To determine the content of DNT and ANT in the hydrogenation bath, samples of suspension were taken at intervals of not more than 4 hours from the line from the stirred tank reactor to the lamellar clarifier. These were freed of suspended solid by filtration and the concentration of the nitro compounds comprised was determined by means of polarography. The DNT concentration was set to from 3 to 30 ppm (on average: 10 ppm) and the aminonitrotoluene concentration was set to from 1 to 200 ppm (on average: 3 ppm) by adjusting the catalyst concentration in the aqueous suspension fed to the reactor (see above).

The reactor was operated under the conditions mentioned for 3 months without significant interruptions. During this time, the crystallite size determined by means of X-ray powder diffraction of the Ni catalyst filtered off in each case from the above samples of suspension increased from 15 nm to 16 nm as a result of sintering. An appreciable change in the stoichiometric composition of the catalyst or its catalytic performance was not observed, nor was formation of oxidized Ni species (for example formation of Ni(OH)$_2$ by oxidative poisoning).

Example 3

The stirred tank reactor described in example 2 was used and the procedure described there was employed. To achieve better separation of the reaction products from the catalyst, to make oxidative poisoning more difficult and achieve optimal homogeneity of the hydrogenation bath even at a lower reaction temperature of from 100 to 105° C., ethanol was used as additional solubilizer. The catalyst was accordingly not introduced in aqueous suspension but instead in the form of 0.5 t/h of an ethanolic suspension (ethanol recovered from the hydrogenation product in the work-up section was mostly used here). The amount of the catalyst comprised in this suspension was varied in a targeted manner in the range from 0 to 5 kg/h as in example 2 in order to set the DNT concentration and was on average just under 1 kg/h. The other flows were as described in example 2.

The about 5.9 t/h of hydrogenation product taken from the lamellar clarifier via the overflow comprised a good 3.3 t/h of TDA (with an isomer distribution corresponding to that of the DNT used), about 0.05 t/h of low and high boilers (in a ratio of about 10:40) and about 2 t/h of water, about 0.5 t/h of ethanol and up to 1 kg/h of catalyst (mostly fines). The hydrogenation product was conveyed via a pressure reduction like the hydrogenation products of other reactors into a joint intermediate vessel and was fed continuously from this to the work-up by distillation. To determine the content of DNT and ANT in the hydrogenation bath, samples of suspension were taken at intervals of not more than 4 hours from the line from the stirred tank reactor to the lamellar clarifier. These were freed of suspended solid by filtration and the concentration of the nitro compounds comprised was determined by means of polarography. The DNT concentration was set to from 3 to 30 ppm (on average: 10 ppm) and the ANT concentration was set to from 1 to 200 ppm (on average: 3 ppm) by adjusting the catalyst concentration in the aqueous suspension fed to the reactor (see above).

The reactor was operated under the conditions mentioned for 3 months without significant interruptions. During this time, the crystallite size determined by means of X-ray powder diffraction of the Ni catalyst filtered off in each case from the above samples of suspension increased from 14 nm to 15 nm as a result of sintering. An appreciable change in the stoichiometric composition of the catalyst or its catalytic performance was not observed, nor was formation of oxidized Ni species (for example formation of Ni(OH)$_2$ by oxidative poisoning).

Example 4

As in example 2, a stirred tank reactor (diameter: 2.8 m, height: 4.7 m, volume: 23 m³, material: St37) having cooling coils fastened in the interior in the region of the reactor wall and a double inclined blade stirrer was used. However, the fastenings of the cooling coils and the nozzle ring for distribution of hydrogen were made very much more solid and thus resulted in slightly poorer mixing of the hydrogenation bath. Otherwise, the reaction was carried out as described in example 2.

Despite an average concentration of the fresh catalyst added to the aqueous suspension which was doubled compared to example 2, viz. 2 instead of 1 kg/h, i.e. introduction of twice as much fresh catalyst, the average aminonitrotoluene concentration in the filtered samples of suspension taken between the reactor and the lamellar clarifier increased, compared to example 2, from 3 to 25 ppm, and values up to 300 ppm were sometimes measured. The average DNT concentration was also slightly increased at 15 instead of 10 ppm, and values up to 50 ppm were sometimes measured.

The reactor was operated under the conditions mentioned for three months, likewise without significant interruptions. During this time, the crystallite size determined by means of X-ray powder diffraction of the Ni catalyst which was in each case filtered off from the above samples of suspension increased very greatly from 8 nm to 17 nm as a result of sintering. An appreciable change in its stoichiometric composition or formation of oxidized Ni species (e.g. formation of Ni(OH)$_2$ by oxidative poisoning) did not occur here either. However, the amount of DNT fed in had to be reduced stepwise after these three months in order to prevent a further increase in the concentration of DNT and aminonitrotoluene. After a further two months, replacement of the entire catalyst was unavoidable.

Comparative Example 1

The stirred tank reactor described in example 4 was used and the procedure described there was employed. In contrast to example 4, the hydrogenation bath here consisted of a mixture of toluenediamine (TDA) and water in a ratio of 0.3:0.7, which apart from the dissolved hydrogen comprised only about 1.5% by weight of the metallic Ni catalyst supported on SiO$_2$ and ZrO$_2$ which was mentioned in example 1 in suspended form. The amount of the fresh catalyst comprised in the aqueous suspension fed in was on average only just under 0.5 kg/h.

The reactor could be operated under these conditions for only about one hour. The reaction then had to be stopped because of a decreasing uptake of hydrogen. The polarographic determination of the content of DNT and aminonitrotoluenes in the filtered sample of the suspension taken from the line from the stirred tank reactor to the lamellar clarifier 30 minutes after commencement of the reaction indicated a DNT concentration of 842 ppm and an aminonitrotoluene concentration of 2050 ppm. Subsequent examination of the Ni catalyst filtered off from a sample of suspension taken after the reaction had been stopped did indicate an unchanged Ni crystallite size and stoichiometric composition within measurement accuracy, but a considerable part of the nickel was present in oxidized form (mostly as catalytically inactive $Ni(OH)_2$). Replacement of the entire catalyst was unavoidable.

Example 5

The hydrogenation of DNT to TDA was carried out in a 180 ml continuous stirred tank, and the catalyst was mechanically held back in the reactor. A 2.8% Pt-0.7% Ni on Norit® SX activated carbon support catalyst (WO 2005/037768) was suspended in water and introduced into the reactor (amount of catalyst=0.5% by weight of the liquid volume of the reactor); the reactor was maintained at a temperature of 125° C. Under a hydrogen pressure of 24 bar, DNT was metered in continuously as a melt in such an amount that a space velocity over the catalyst of 180 $kg_{DNT}/kg_{cat}.h$ was set. Samples were analyzed by means of gas chromatography: the DNT and ANT concentration and the TDA yield were monitored.

Example 6

Same as example 5 but with a space velocity over the catalyst of 229 $kg_{DNT}/kg_{cat}.h$.

Comparative Example 2

Same as example 5 but with a space velocity over the catalyst of 45 $kg_{DNT}/kg_{cat}.h$.

Comparative Example 3

Same as example 5 but with a space velocity over the catalyst of 284 $kg_{DNT}/kg_{cat}.h$.

|  | TDA yield (%) | DNT (ppm) | ANT (ppm) |
| --- | --- | --- | --- |
| Example 5 | 99.1 | 29 | 600 |
| Example 6 | 98.5 | 127 | 2450 |
| Comparative example 2 | 98.7 | 0 | 0 |
| Comparative example 3 | 96.4 | 1000 | 19500 |

Example 7

The hydrogenation of DNT to TDA was carried out in a 180 ml continuous stirred tank, and the catalyst was mechanically held back in the reactor. A catalyst as described in example 1 was suspended in water and introduced into the reactor (amount of catalyst=2.5% by weight of the liquid volume of the reactor), and the reactor was maintained at a temperature of 125° C. Under a hydrogen pressure of 24 bar, DNT was metered in continuously as a melt in such an amount that a space velocity over the catalyst of 17 $kg_{DNT}/kg_{cat}.h$ was set. Samples were analyzed by means of gas chromatography: the DNT and ANT concentration and the TDA yield were monitored.

Comparative Example 4

Same as example 6 but with a space velocity over the catalyst of 12 $kg_{DNT}/kg_{cat}.h$.

|  | TDA yield (%) | DNT (ppm) | ANT (ppm) |
| --- | --- | --- | --- |
| Example 7 | 99.4 | 15 | 300 |
| Comparative example 4 | 98.3 | 0 | 0 |

Comparison of Different Analytical Methods for Determining DNT and ANT:

Three methods for the analysis of DNT and ANT in the hydrogenation bath are, by way of example, described and compared below. For this purpose, a series of experiments was set up and the analytical methods were compared. The examples described are intended to show that it is possible to analyze the hydrogenation bath using conventional analytical methods and that the same results are obtained regardless of the method of analysis. The three methods gas chromatography (GC), high-pressure liquid chromatography (HPLC) and polarography are only examples of the large number of different possible spectroscopic, chromatographic, electrochemical and other methods. It can be seen from the following results that, for example, the use of polarography is possible in principle but it has to be ensured that the samples are measured promptly (at the latest 4 hours, better 1 hour, even better 30 minutes or 15 minutes, after sampling). Otherwise, DNT and ANT values which are erroneously too high are obtained. GC and HPLC enable the substances to be identified and quantified without erroneously positive results being obtained.

The analytical methods are preferably carried out as follows:

Polarography is carried out in a solvent mixture consisting of equal parts of dimethylformamide and 1 mol/l chloric acid solution.

In the electrolyte indicated, dinitrotoluene (DNT) is reduced at about 330 mV and aminonitrotoluene is reduced at about 550 mV. A change in the isomer ratio does not influence the height of the polarographic step.

VA-processor 746 or 693 polarograph with VA stand (from Metrohm)
Dropping mercury electrode, DME,
Reference electrode, Ag/AgCl,
Electrolyte key, saturated LiCl in ethanol,
Volumetric flasks 100 ml, 50 ml and 25 ml,
Analytical balance (reading precision 0.001 g or better), e.g. Sartorius RC 250
Pipette 5 ml,
Titration vessels Gas chromatography (GC) is preferably carried out as indicated below:
Column: Varian—Factor Four CP 8977 (10 m×0.10 mm ID×0.20 µm FT)
Carrier gas: helium
Pressure: 41.8 psi
Split flow: 15.2 ml/min
Temperature (ECD): 300° C.
Temperature (injector): 250° C.
Oven: initial temp.: 75° C.-20.0° C./min→250° C.-4.0 min
Injection volume: 0.2 µl
Sample preparation: sample weight: about 500 mg+5 ml of MeOH High-pressure liquid chromatography (HPLC) is preferably carried out as follows:
Column: Agilent Lichrosorb RP-18 (4.6×200 mm, 5 μm)
Eluent 1: water+1 g/l of ammonium acetate
Eluent 2: methanol
Gradient: 0 min 70% of water/30% of methanol
18 min 10% of water/90% of methanol
25 min 10% of water/90% of methanol
30 min 70% of water/30% of methanol
Flow: 0.5 ml/min
Oven temp.: 38° C.
Wavelength: 254 nm/bandwidth 4 nm, reference 550 nm/bandwidth 100 nm
Inj. volume: 25 μl
Sample preparation: weight of sample: about 500 mg+5 ml of MeOH
Series of Experiments:

Mixtures of precisely 60.00 g of freshly distilled TDA (2,4- and 2,6-isomer) and 40.00 g of water were produced in a 250 ml conical flask and mixed well at 85° C. As soon as the samples were homogeneous, various amounts of a DNT isomer mixture were added and the samples were homogenized again. The content of the 2,4-DNT isomer was then determined by means of GC and HPLC and the total content of all DNT isomers was determined by means of GC and polarography. The determination by means of polarography was carried out 15 minutes after the renewed homogenization and a second time 4 hours after the renewed homogenization.

Results (Measured Values in ppm):

| Sample | Method | | 2,4-DNT | Total DNT |
|---|---|---|---|---|
| 0 | GC | | 0 | 0 |
| | HPLC | | 0 | |
| | Polarography | After 15 min | | 0 |
| | | After 4 h | | 45 |
| 1 | GC | | 18 | 20 |
| | HPLC | | 17 | |
| | Polarography | After 15 min | | 19 |
| | | After 4 h | | 34 |
| 2 | GC | | 39 | 46 |
| | HPLC | | 37 | |
| | Polarography | After 15 min | | 49 |
| | | After 4 h | | 69 |
| 3 | GC | | 55 | 65 |
| | HPLC | | 53 | |
| | Polarography | After 15 min | | 60 |
| | | After 4 h | | 75 |

The invention claimed is:

1. A process for the continuous preparation of toluenediamine by liquid-phase hydrogenation of dinitrotoluene by means of hydrogen in the presence of a suspended, nickel-comprising catalyst in a reactor with a product isolation unit downstream of the reactor to give a product output from the reactor comprising a liquid phase comprising toluenediamine and dinitrotoluene, in which the nickel-comprising catalyst is suspended, wherein the concentration of dinitrotoluene in the liquid phase of the product output from the reactor in the region between the reactor and the downstream product isolation unit is set to a value in the range from 1 to 200 ppm by weight, based on the total weight of the liquid phase of the product output from the reactor,
wherein the setting of the dinitrotoluene concentration in the liquid product output from the reactor in the region between the reactor and the downstream product isolation unit is carried out on the basis of a repeated measurement of the dinitrotoluene concentration in the liquid product output from the reactor at time intervals of ≤24 hours.

2. The process according to claim 1, wherein the concentration of dinitrotoluene in the liquid product output from the reactor is set to a value in the range from 1 to 100 ppm by weight, based on the total weight of the liquid product output from the reactor.

3. The process according to claim 1, wherein the hydrogenation of dinitrotoluene to toluenediamine is carried out at a temperature in the range from 50 to 250° C.

4. The process according to claim 1, wherein the hydrogenation of dinitrotoluene to toluenediamine is carried out at a pressure in the range from 5 to 50 bar.

5. The process according to claim 1, wherein the liquid phase of the product output comprises aminonitrotoluene and the concentration of aminonitrotoluene in the liquid phase of the product output from the reactor in the region between the reactor and the product isolation unit is set to a value in the range from 0 to 2000 ppm by weight, based on the total weight of the liquid phase of the product output.

6. The process according to claim 1, wherein the reactor is selected from the group consisting of a stirred tank reactor, a loop reactor and a bubble column.

7. The process according to claim 1, wherein the reactor is a jet loop reactor having external and internal circulation.

8. The process according to claim 1, wherein the product isolation unit is selected from the group consisting of a filter, a static decanter and a dynamic decanter.

9. The process according to claim 1, wherein the suspended catalyst comprises at least one metal of transition groups I., II., V., VI. and/or VIII. of the Periodic Table in addition to nickel as catalytically active metal.

10. The process according to claim 1, wherein the catalyst has a nickel content in the range from 0.1 to 99% by weight, based on the total weight of the catalyst.

11. The process according to claim 1, wherein the catalyst comprises at least one oxidic support component.

12. The process according to claim 1, wherein the catalyst comprises platinum and nickel.

13. The process according to claim 1, wherein the catalyst comprises palladium, nickel and iron.

14. The process according to claim 1, wherein the catalyst is used in an amount of from 0.1 to 15% by weight, based on the total weight of the reaction mixture in the reactor.

15. The process according to claim 1, wherein the reaction is carried out in a three-phase mixture composed of hydrogen-comprising gas phase, suspended catalyst and liquid phase comprising from 0 to 40% by volume of an alcohol, from 10 to 60% by volume of water and from 20 to 70% by volume of toluenediamine.

16. The process according to claim 1, wherein the concentration of dinitrotoluene in the liquid product output from the reactor is set to a value in the range from 3 to 30 ppm by weight, based on the total weight of the liquid product output from the reactor.

17. The process according to claim 1, wherein the dinitrotoluene concentration in the liquid phase product output is set repeatedly at a time interval of ≤4 hours.

18. A process for continuously forming toluene diamine, comprising:
(i) liquid-phase hydrogenating dinitrotoluene with hydrogen in the presence of a suspended nickel-comprising catalyst,
wherein the liquid-phase hydrogenating is carried out in a reactor connected to a product isolation unit downstream of the reactor, wherein the liquid-phase hydrogenating forms a liquid phase product output comprising toluene diamine, dinitrotoluene, and the nickel-comprising catalyst, wherein the nickel-comprising catalyst is suspended in the liquid-phase product output, (ii) controlling the concentration of the dinitrotoluene in the liquid phase product output after the reactor and before the product isolation unit at a concentration of from 1 to 200 ppm by weight based on the total weight of the liquid phase product output, wherein the concentration of the dinitrotoluene in the liquid phase product output is repeatedly controlled at a time interval of ≤24 hours during the liquid-phase hydrogenating.

19. The process according to claim 18, wherein the dinitrotoluene concentration in the liquid phase product output is controlled repeatedly at a time interval of ≤4 hours.

* * * * *